United States Patent [19]
Salvadori

[11] Patent Number: 5,931,303
[45] Date of Patent: *Aug. 3, 1999

[54] COMPACT, POCKETED WRAPPING FOR A MEDICAL PROCEDURE KIT AND PROCESS FOR USING SAME

[76] Inventor: Lawrence A. Salvadori, 11434 Duenda Rd., San Diego, Calif. 92127

[ * ] Notice: This patent issued on a continued prosecution application filed under 37 CFR 1.53(d), and is subject to the twenty year patent term provisions of 35 U.S.C. 154(a)(2).

[21] Appl. No.: 08/723,788

[22] Filed: Sep. 30, 1996

[51] Int. Cl.⁶ .................................................. B65D 69/00
[52] U.S. Cl. .......................... 206/570; 206/363; 206/373; 383/39; 229/87.1
[58] Field of Search ................................ 206/570, 571, 206/363, 364, 370, 372, 373, 438, 410, 440, 278; 383/39, 38, 88, 40, 4; 229/87.5, 87.01, 87.15, 87.16; 53/593, 430, 116, 117, 118, 216; 493/308, 198

[56] References Cited

U.S. PATENT DOCUMENTS

| | | |
|---|---|---|
| 34,117 | 1/1862 | McEroy ..................................... 383/39 |
| 36,710 | 10/1862 | Hamlin ...................................... 383/39 |
| 3,086,572 | 4/1963 | Lubin ........................................ 383/39 |
| 3,583,391 | 6/1971 | Cox et al. . |
| 3,620,439 | 11/1971 | Morse et al. . |
| 3,752,158 | 8/1973 | Kariher . |
| 3,770,119 | 11/1973 | Hlutberg et al. . |
| 3,826,421 | 7/1974 | Morse et al. . |
| 3,854,483 | 12/1974 | Powers . |
| 3,888,234 | 6/1975 | Clark . |
| 3,978,983 | 9/1976 | Brezette . |
| 4,099,614 | 7/1978 | Heissenberger .......................... 206/438 |
| 4,149,635 | 4/1979 | Stevens . |
| 4,160,505 | 7/1979 | Rauschenberger . |
| 4,170,996 | 10/1979 | Wu . |
| 4,210,244 | 7/1980 | Westrick ................................ 206/370 |
| 4,230,115 | 10/1980 | Walz, Jr. et al. . |
| 4,342,390 | 8/1982 | Mitchell et al. ......................... 206/363 |
| 4,501,584 | 2/1985 | Cianci et al. . |
| 4,503,864 | 3/1985 | Powers . |
| 4,523,679 | 6/1985 | Paikoff et al. .......................... 206/570 |
| 4,583,643 | 4/1986 | Sanderson . |
| 4,716,025 | 12/1987 | Nichols . |
| 4,754,595 | 7/1988 | Sanderson . |
| 4,811,847 | 3/1989 | Reif et al. . |
| 4,944,427 | 7/1990 | Yamada et al. . |
| 5,022,521 | 6/1991 | Kane ....................................... 206/370 |
| 5,031,768 | 7/1991 | Fischer . |
| 5,080,874 | 1/1992 | Nichols . |
| 5,082,111 | 1/1992 | Corbitt, Jr. et al. ..................... 206/363 |
| 5,163,950 | 11/1992 | Pinchuk et al. . |
| 5,183,643 | 2/1993 | Nichols . |
| 5,242,398 | 9/1993 | Knoll et al. . |
| 5,454,797 | 10/1995 | Haswell . |
| 5,460,606 | 10/1995 | Daneshvar . |

*Primary Examiner*—Paul T. Sewell
*Assistant Examiner*—Nhan T. Lam
*Attorney, Agent, or Firm*—David J. Koris

[57] ABSTRACT

A sterile, compact wrapping is provided to present components in order of use in a medical procedure, particularly a urethral catheterization procedure. Pockets are arranged in a line along a longitudinally extending midsection of the wrapping. Longitudinally extending flaps are provided along the edges of the midsection. Components are placed in the pockets in order of use, and the wrapping is rolled up, beginning with the pocket containing the last used component. The flaps are folded over the rolled up midsection. The rolled and folded wrapping, which maintains the components in a sterile condition until use, may be placed in a further package for shipping. In use, the flaps are unfolded and the wrapping is unrolled sufficiently to expose the first needed component. As the procedure continues, the wrapping is unrolled sufficiently to expose the next needed component, until all components have been used. The used components may be replaced in the pockets and the wrapping rerolled and refolded for disposal.

14 Claims, 2 Drawing Sheets

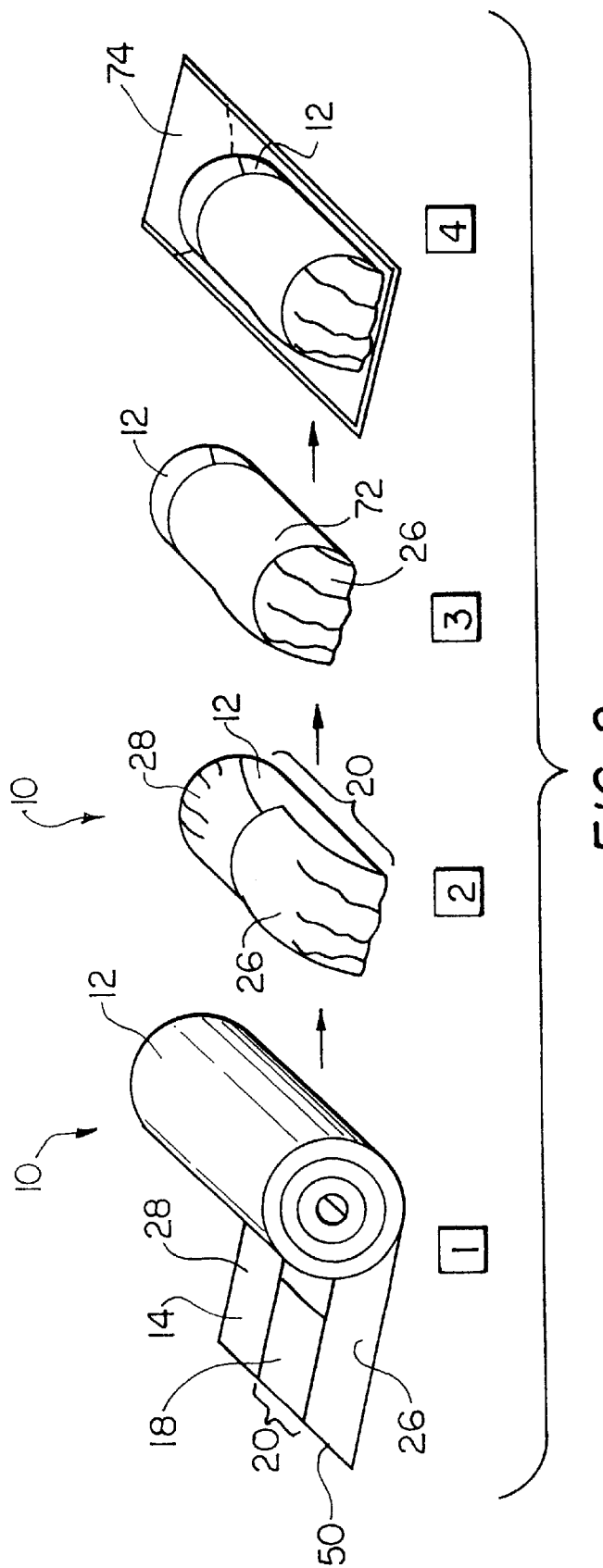

5,931,303

COMPACT, POCKETED WRAPPING FOR A MEDICAL PROCEDURE KIT AND PROCESS FOR USING SAME

FIELD OF THE INVENTION

This invention relates to medical devices provided in kits or trays for performing a medical procedure and more particularly to urethral catheter kits.

BACKGROUND OF THE INVENTION

A urethral catheter kit or tray is used to catheterize a patient on a short term basis to void the bladder, the catheter being removed immediately thereafter. The kit includes an underpad, gloves, a fenestrated drape, lubricating gel, swab sticks, a catheter, and a collection bag. The kit is typically called a tray, because the components are supplied in a tray-like device. The tray with the components placed therein is usually wrapped with a piece of CSR wrap (combined paper tissue and plastic sheeting) to provide a barrier to gross contamination. The components are arranged only generally in order of their use in the procedure and can become disarranged or damaged by moving around.

BRIEF SUMMARY OF THE INVENTION

The present invention provides a kit for a medical procedure, particularly a urethral catheterization procedure, which presents components to be used in the procedure in their exact order of use, while maintaining the components in a clean condition until the moment they are needed. The kit is of a compact size, occupying approximately 50 percent of the volume occupied by prior art catheterization trays. The components are retained more securely in place, minimizing the risk of damage due to movement during shipping or use.

More particularly, the kit comprises a wrapping comprising a first layer of a flexible sheet material which forms a barrier to gross contamination. The first layer comprises a longitudinally extending midsection and first and second longitudinally extending flaps arranged on opposed, longitudinally extending sides of the midsection. A further flexible sheet material is attached to the midsection of the first layer along seams to define pocket perimeters. The pockets are individually sized to receive specified components used in the medical procedure. The pockets are arranged generally linearly from one end of the midsection to the other in the exact order in which their associated components are to be used.

Under normal assembly room conditions, the pockets are loaded with their associated components. The wrapping is rolled up about an axis transverse to the longitudinal extent of the wrapping, starting with the end nearest the pocket containing the last-used component. The flaps are then folded over the midsection to close off the wrapping, thereby forming a package which can maintain the components in a clean condition. The rolled and folded wrapping may be placed in a further container, such as a paper wrapper and/or sealed plastic bag, for shipment and storage.

In use, the wrapping is removed from the further container, and the flaps are unfolded. The wrapping is then gradually unrolled to expose only the component needed at the moment. In this manner, the remaining components are maintained in a clean condition until the moment of use. After use, the components may be replaced in their pockets and the wrapping rerolled and refolded for disposal in a suitable manner.

BRIEF DESCRIPTION OF THE SEVERAL VIEW OF THE DRAWING

The invention will be more fully understood from the following detailed description taken in conjunction with the accompanying drawings in which:

FIG. 1 is a perspective view of a wrapping for a urethral catheter kit in an unrolled configuration according to the present invention; and FIG. 2 is a schematic view of a process for assembly of the urethral catheter kit of FIG. 1.

DETAILED DESCRIPTION OF THE INVENTION

Figure 1:
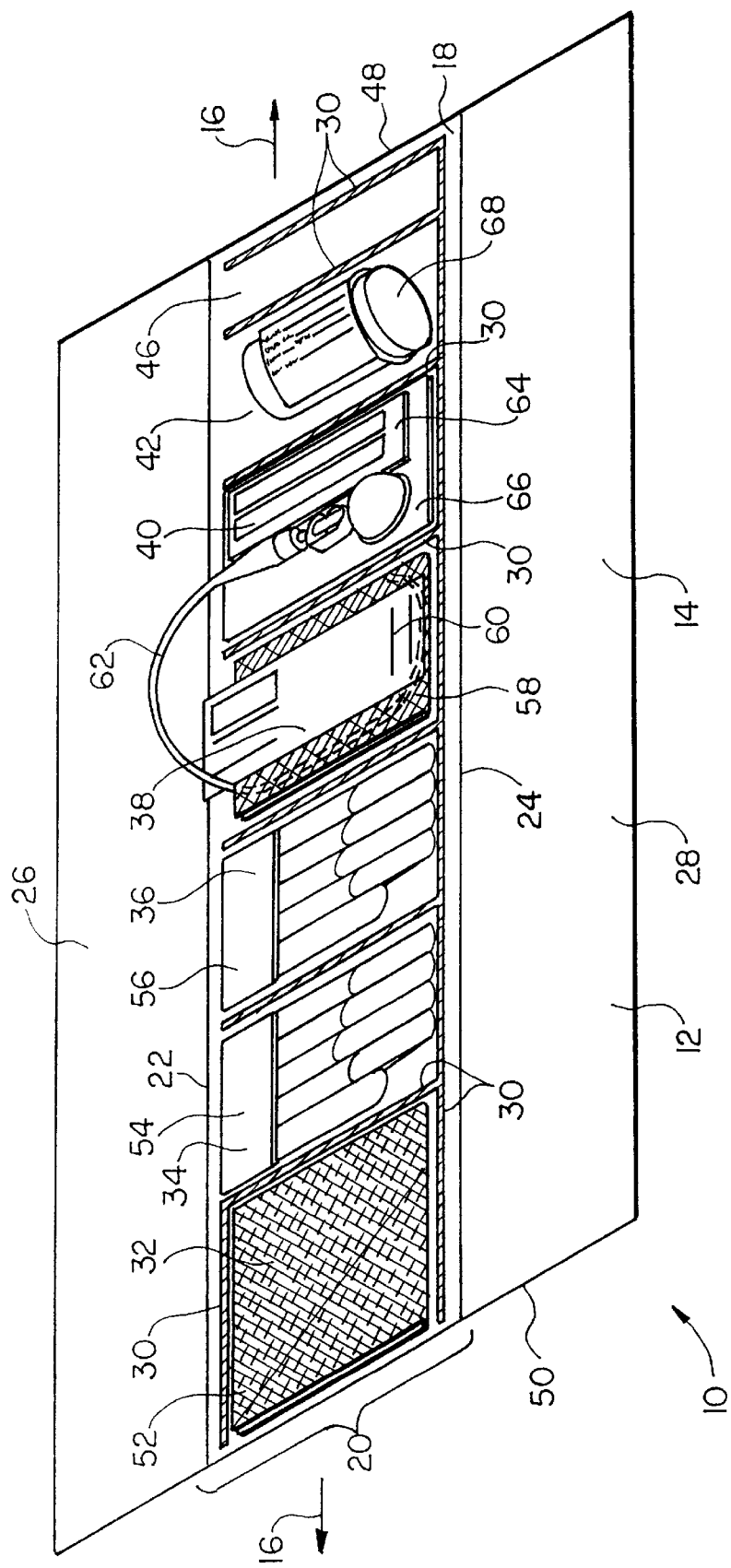

Referring to FIG. 1, a urethral catheterization kit 10 in an unfolded and unrolled configuration is shown. The kit comprises a wrapping 12 which is formed of a first layer 14 of a flexible sheet material. In the preferred embodiment, the layer 14 is provided in a generally rectangular configuration having a length dimension defining a longitudinal axis, indicated by arrows 16, and a width dimension defining a transverse axis perpendicular to the longitudinal axis.

The kit also includes a second layer 18 of a flexible sheet material which is attached, discussed further below, to the first layer in a midsection 20 of the first layer 14. The second layer 18 typically has a rectangular configuration having a length dimension generally equal to the length dimension of the first layer and a width dimension smaller than the width dimension of the first layer, the width dimension defining the width of the midsection 20. Those portions of the first layer which extend transversely beyond the longitudinal edges 22, 24 of the second layer 18 form first and second longitudinally extending flaps 26, 28 arranged on opposed, longitudinally extending sides of the midsection, for a purpose discussed further below. The first and second layers 14, 18 can be formed of a suitable material capable of providing a substantially gas and particle impermeable barrier and maintaining clean conditions inside the wrapping 12 when the wrapping is rolled and folded, as discussed further below. The second layer 18 should be a transparent material, for a purpose discussed further below. The inside surface of the first layer 14 must be wettable to preclude liquid droplets from rolling off the wrapping during use in a medical procedure. For example, a polymer such as polyethylene with a proper surface finish could be used.

The second layer 18 is attached to the first layer 14 along seams 30 which define pocket perimeters, thereby forming pockets 32, 34, 36, 38, 40, 42, 44, 46 in the region between the first and second layers of the wrapping. Typically, each pocket is defined by three seams forming three sides of the pocket. The seams can be formed in any suitable manner, for example, by heat sealing, adhesive bonding, RF or sonic welding, or stitching. Heat sealing is preferred for plastic sheeting, since it requires the shortest cycle times, allowing production of the maximum number of units per unit time. The pockets 32, . . . , 46 are arranged in a line from a first transverse end 48 of the wrapping 12 to a second transverse end 50 of the wrapping. In the presently preferred embodiment, the pocket 32 closest to the second end 50 opens along the second end, as discussed further below. The remaining pockets have openings extending normal to the longitudinal axis of the wrapping. The material forming the second layer may be transparent to allow the components in the pockets to be seen. The pockets 32, . . . , 46 are selectively sized to retain the components used in a particular medical procedure in the order of use. For example, for the urethral catheterization procedure, the first pocket 32 contains an underpad 52, the first component used in the procedure. The next two pockets 34, 36 contain latex examination gloves 54, 56, which are used next. The fourth pocket 38 contains a fenestrated drape 58 and swab sticks 60. A catheter 62 may be placed in both the fourth pocket 38 and the fifth pocket 40, as illustrated, or in a single pocket. The fifth pocket 40 contains lubricating gel 64 and a collection bag 66. The sixth pocket 42 contains a specimen bottle 68. In the embodiment shown, a seventh pocket 46 is shown. This pocket can contain any other suitably-sized component or left empty. As is apparent, any single pocket can contain one or more components or no components. It will also be appreciated that the number and size of the pockets will be selected to suit the particular medical procedure for which the wrapping is intended to be used.

In assembly of the wrapping 12 into a medical procedure kit 10, the medical components are placed in the appropriate pockets in the order of use beginning at one end of the wrapping. Typically, the first item used is placed in the pocket 32 which opens along the transverse end 50 of the wrapping. The wrapping 12 is then rolled up, as shown more particularly in FIG. 2, beginning at the end 48 closest to the pocket containing the last item used, for example, the specimen bottle 68 in the sixth pocket 42 in the illustrated catheterization example. After the wrapping is fully rolled up, the flaps 26, 28 are folded down over the midsection 20 of the wrapping 12, as shown in the second illustration in the sequence of FIG. 2. The flaps are sufficiently wide in the transverse direction to provide a complete closure of the sides of the midsection. In this manner, the folded flaps provide a closure for the wrapping to keep gross contaminants away from the components inside the wrapping. Generally, the flaps are sufficiently wide such that at least a portion of the opposed flaps overlap when folded, thereby covering substantially all of the midsection. Also, the flaps are preferably folded to cover the second end 50, which is the exposed end when the wrapping is rolled, to prevent contaminants from entering this end. The wrapping 12 may be placed in a further container for shipping and storage, if desired. For example, the folded and rolled wrapping may be placed in a paper wrapper 72, which serves to retain the flaps in the folded configuration, and then in a sealed plastic bag 74, which serves to maintain the wrapping in a sterile condition, as shown in the third and fourth illustrations of FIG. 2.

In use, the wrapping 12 is removed from the sealed plastic bag 74 and the paper wrapper 72. The wrapping is placed on a work surface and the flaps 26, 28 are unfolded. The wrapping is then unrolled sufficiently to expose only the first component or components needed at that particular moment in the procedure, such as the underpad 52. The remaining components are maintained in a clean condition inside the rolled portion of the wrapping. As the next component(s) is needed, the wrapping is unrolled sufficiently to expose only that component(s). The procedure is continued in this manner, unrolling only that portion of the wrapping necessary to expose the component(s) needed at the particular moment in the procedure, until the procedure has been completed. The used components can be replaced in their associated pockets in the wrapping and the wrapping can be rerolled and refolded for disposal in a suitable manner.

The medical procedure kit of the present invention is advantageous in that it occupies less volume than typical prior art kits. For example, when used for a urethral catheterization kit, the invention occupies approximately 50 percent of the volume occupied by prior art catheterization trays. The kit maintains the components in a clean condition until the moment of use, and the components are presented in their order of use. The procedure can thereby occur in a more orderly manner with less risk of premature contamination of the components. The components are retained more securely in place, minimizing the risk of damage due to movement during shipping or use.

The invention is not to be limited by what has been particularly shown and described, except as indicated by the appended claims.

What is claimed is:

1. A kit for a medical procedure, the kit comprising:
   a wrapping comprising in an unrolled configuration:
      a first layer of a flexible sheet material, the first layer having a generally rectangular configuration defining a longitudinal axis,
      the first layer further comprising a longitudinally extending midsection and first and second longitudinally extending flaps arranged on opposed, longitudinally extending sides of the midsection, and
   a plurality of pockets arranged within the midsection in a line along the longitudinal axis, the pockets formed by a second layer of a flexible sheet material attached to the first layer along seam lines to define pocket perimeters;
   wherein the wrapping is rolled up about an axis transverse to the longitudinal axis beginning with a first end, and wherein the flaps are folded as a roll over the rolled up midsection; and
   wherein a plurality of components for a medical procedure are disposed in the pockets in order of use with the first component to be used in the pocket nearest a second end of the wrapping and the last component to be used in the pocket nearest the first end of the wrapping.

2. The kit of claim 1, further comprising a outer package disposed over the rolled and folded wrapping.

3. The kit of claim 2, wherein the outer package comprises a paper wrapper.

4. The kit of claim 2, wherein the outer package comprises a sealed plastic bag.

5. The kit of claim 1, wherein each of the first and second flaps has a transverse width sufficient to cover the midsection sides when the midsection is in a rolled configuration.

6. The kit of claim 1, wherein the first layer comprises a plastic material.

7. The kit of claim 1, wherein the second layer comprises a plastic material.

8. The kit of claim 1, wherein a first pocket of the plurality of pockets is disposed at the second end of the wrapping.

9. The kit of claim 8, wherein the first pocket has an opening extending along the second end of the wrapping.

10. The kit of claim 1, wherein at least one pocket has an opening extending normal to the longitudinal axis.

11. The kit of claim 1, wherein the plurality of pockets extends from the first end to the second end of the wrapping.

12. The kit of claim 1, wherein the second layer of the flexible sheet material is heat sealed to the first layer along the seam lines to form the plurality of pockets.

13. The kit of claim 1, wherein each of the pockets of the plurality of pockets are sized to receive a specified component of a urethral catheter kit.

14. The kit of claim 1, wherein the first layer is formed from a material capable of providing a barrier to gross contamination.

* * * * *